United States Patent [19]  [11] 4,107,207
Holmes  [45] Aug. 15, 1978

[54] MIXED METAL AMIDE CATALYSTS FOR H-D EXCHANGE IN AMINES

[75] Inventor: John M. Holmes, Sarnia, Canada

[73] Assignee: Atomic Energy of Canada Limited, Ottawa, Canada

[21] Appl. No.: 820,876

[22] Filed: Aug. 1, 1977

[30] Foreign Application Priority Data

Aug. 3, 1976 [CA] Canada .................................. 258321

[51] Int. Cl.$^2$ ............................................. C07C 83/00
[52] U.S. Cl. .............................. 260/583 R; 252/431 N
[58] Field of Search ................. 260/583 R; 252/431 N

[56] References Cited

U.S. PATENT DOCUMENTS 3,510,519   5/1970   Frejaville et al. ............... 260/583 R

FOREIGN PATENT DOCUMENTS 719,200   10/1965   Canada ......................... 260/583 R UX Primary Examiner—Paul F. Shaver
Attorney, Agent, or Firm—Alan A. Thomson

[57] ABSTRACT

A catalyzed process for deuterium isotope enrichment by H-D exchange between an amine and hydrogen in which the exchange catalyst includes a mixture of Group I and Group II metal amides. Catalyst mixtures of potassium methylamide with beryllium, calcium or strontium methylamide are of particular interest. Resistance to hydride formation is equivalent to the binary Group I metal amide catalysts and higher H-D exchange rates can be achieved with some combinations.

17 Claims, No Drawings

MIXED METAL AMIDE CATALYSTS FOR H-D EXCHANGE IN AMINES

This invention is concerned with composite catalysts for H-D exchange between hydrogen and an amine leading to deuterium enrichment (usually for the production of heavy water).

It is known to contact a hydrogen stream carrying input deuterium with an organic amine phase in a catalyzed exchange process to ultimately yield a stream of hydrogen or amine enriched in deuterium. Dissolved alkali metal alkylamide has been used as exchange catalyst in such a process in Canadian Pat. No. 719,200, Oct. 5, 1965 Klein et al. These single alkali metal alkylamide-in-amine combinations all have drawbacks that tend to make them impractical for commercial process operation. These drawbacks usually fall into three categories:

1. catalyst thermal decomposition and/or hydrogenolysis to precipitate hydride,
2. low catalyst solubility in amine, or
3. low exchange rate.

Many of the disadvantages of the single alkali metal alkylamide catalyst can be overcome by the use of mixed alkali metal alkylamide catalysts especially mixed lithium and potassium alkylamide (see Canadian application No. 177,785, filed July 31, 1973 W. J. Holtslander and R. E. Johnson). While the decomposition and hydrogenolysis problem can be largely solved by these mixed alkali metal alkylamide systems, an increase in catalytic activity or exchange rate would be desirable.

It has now been found that certain Group II metals (of the Periodic Table) will form composite amides with Group I metals the composite being selected to have desirable catalytic activity, (in some cases improved catalytic activity over binary Group I metal alkylamide catalysts) and resistance to hydride formation. These composite catalysts have been found to have improved stability compared to the single alkali metal alkylamide catalyst, while their thermal stability appears only slightly lower than for the binary Group I metal alkylamide. Resistance to hydrogenolysis and hydride precipitation is at least equivalent to that of the binary Group I metal alkylamide.

Thus the invention includes a process for catalyzed H-D exchange between hydrogen and an amine in a deuterium enrichment process comprising utilizing as catalyst in the amine phase a dissolved composite amide including both Group I metal and Group II metal amides, the composite catalyst being selected to provide at least one of an increased H-D exchange rate or prolonged activity over that of the signle Group I metal amide; and the novel composite catalyst composition.

Simple Group II metal methylamides have been investigated and found to be difficult to prepare, of low solubility in the amine and their solutions are susceptible to mechanical and thermal shock. On this basis they are judged unsuitable per se as catalysts for H-D exchange.

While single Group II metal alkylamides are difficult or practically impossible to prepare, mixed Group I plus Group II metal amides can be prepared for all members of Group II. Amides of Be, Mg, Ca, Sr and Ba have been prepared in conjunction with Group I metal amides. The preferred method of preparation is the treatment of the Group II metal with the alkali metal alkylamide in alkylamide solvent. Not all binary Group I – Group II metal amides have been found to have useful catalytic activity for H-D exchange. For instance the K-Mg alkylamide, Li-Sr alkylamide, and Na-Sr alkylamide tested did not possess adequate H-D exchange activity. The highest exchange rates have been found with K-Sr alkylamide, followed by K-Ca alkylamide and K-Be alkylamide. A k-Ba alkylamide is expected to have useful activity, but the solubility of both Ba methylamide and K-Ba methylamide was found to be low. In all cases the Group I – Group II binary methylamides gave no apparent reaction with hydrogen at 600 psi partial pressure. Both the Group I and the Group II metal should be selected so that the combination has useful H-D exchange catalytic activity and stability.

The amounts of metal alkylamide used as catalyst in the amine will suitably approach the saturation amount for the particular system and conditions, although useful exchange rates can be achieved at concentrations considerably below the saturation level. Sufficient composite amide catalyst should be present in solution to give a useful H-D exchange rate.

The relative amounts of Group I and Group II metals are not sharply critical: the Group II metal will be present in amounts sufficient to accomplish at least one of (a) substantial decrease in hydride formation, and (b) increase in H-D exchange rate (activity), compared to the single Group I metal. Usually the Group II metal will be present in up to about equimolar amounts with the Group I metal. Amounts of Group II metal as low as about 10 mole % of the Group I metal will show useful benefit. Preferably the Group II metal is present in about 30 – 60 mole % based on the Group I metal.

The amine will most suitably be methylamine (and the alkylamides the methylamides): however it is within the scope of the invention to utilize other amines, particularly alkylamines both primary and secondary, and alkyldiamines (see Klein et al above and Canadian Pat. No. 901,266, May 30, 1972, Bancroft et al.). The alkyl groups involved in the amines (or amides) may have one to five carbon atoms in straight or branched chains. Such other amines include dimethylamine; aminoethane; 2-aminopropane; 1,2-diaminoethane and 1,2-diaminopropane. It has been found advantageous in some cases to add pyrrolidine to the amine + metal amide system to increase the exchange rate activity thereof. Selected amounts of pyrrolidine may be added in molar proportions up to about 3 times the molar amount of metal present. Preferably this selected amount is no greater than twice the metal content on a mole to mole basis. Screening is readily done to determine the most appropriate amount for each system.

The following examples are illustrative of suitable composite catalysts. Other catalytic mixed Group I – Group II metal amides than those specifically mentioned as examples are within the scope of the invention.

Calcium and barium (the Ca as metal and the barium as hydride) were found to react with methylamine to form what was believed to be the corresponding metal amide. However, magnesium and strontium showed little or no reaction with methylamine.

Mixed methylamides of, K & Mg (1.1), K & Ca (1.2), K & Ba (1.3), Na & Sr (1.4), Li and Sr (1.5), were prepared by reacting the Group II metal with methylamine solutions of alkali methylamide at room temperature.

These mixed amides are believed to be complexes of the type, e.g., $K_xCa_y(NCH_3)_{x+y+1}$ where $x$ and $y$ depict the relative molar amounts of the K and Ca.

These mixed metal methylamides were tested for H-D exchange activity and hydrogenolysis. The H-D exchange cell was designed by W. J. Holtslander Chem. Eng. Division, CLNL, AECL. It is based on designs by E. Rochard, Commis. Energy At., Rapp 1969, CEA-R-3835 and E. Rochard and J. Ravoire J. Chim. Phys. Physiochim. Biol. 1971. Also mixed methylamide/ pyrrolidide systems were evaluated. The results are summarized in Table 1.

1.1 Potassium magnesium methylamide system

Magnesium metal reacted readily with potassium methylamide (PMA) solution. A deep blue solution was formed which rapidly decayed to give a colourless solution containing a small quantity of fine black powder.

A system designed to contain Mg, 0.5; and K, 0.5 m mole/g was filtered to remove black powder (presumably an impurity from the magnesium metal). The solution gave an exchange rate of 4 min$^{-1}$, and contained K, 0.31; Mg, 0.74; methylamide (MA'), 1.39 m mole/g.

Another preparation gave a solution which had an exchange rate of 9 min$^{-1}$ and contained K, 0.44; Mg, 0.40; MA', 1.13 m mole/g. K:Mg:MA' ratio is 1.1:1.0:2.8. KMg(MA')$_3$ requires a ratio of 1:1:3.

The solution remained clear when treated with hydrogen at 600 psi partial pressure.

A solution to which pyrrolidine was added remained water white. Most methylamide systems (while being at least a pale straw colour to start with) developed a very distinct yellow or orange colour in these circumstances.

1.2 Potassium calcium methylamide systems

1.2.1 Potassium calcium trimethylamide — from calcium dimethylamide and potassium methylamide.

Calcium dimethylamide, Ca(MA')$_2$, which had been prepared from calcium metal and methylamine in its methylamine-insoluble form was treated with an equimolar quantity of PMA. A pale green/yellow solution formed immediately which contained by preparation Ca, 0.5; K, 0.5 m moles/g. Analysis of the solution showed it contained Ca, 0.49; K, 0.43; and MA', 1.36 m mole/g. The K:Ca:MA' ratio was 1:1.1:3.2. The solution on storage at 20° C gradually deposited a white solid.

1.2.2 Dipotassium calcium tetramethylamide — systems containing Ca, 0.25; K, 0.5 m mole/g.

Calcium metal reacted rapidly with PMA at 20° C. This was accompanied by vigourous gas evolution and a dark blue solution was formed, which decolourized rapidly when the calcium metal was consumed. Filtration to remove some fine black powder gave a pale green/yellow solution (a system derived from calcium, 0.43 g, and PMA, 42 g of a 0.5 m mole/g solution gave 38 mg of black material). A Ca/K system prepared in this way was apparently stable at −10° C. Exchange rates on duplicate preparations were 118 and 132 min$^{-1}$ respectively. Analysis of the solute showed it contained K, 0.48; Ca, 0.23; MA', 1.0 m mole/g. The ratio K:Ca:MA' was 2:1:4.35. K$_2$Ca(MA')$_4$ requires a ratio 2:1:4.

Storage of the k, 0.5; Ca, 0.25 m mole/g solution at 20° C caused a colour change to pale yellow (straw) and precipitation of a white solid. Thus 42 g of the freshly prepared solution after 24 hrs at 20° C gave 0.81 g of white solid. This solid material on separately prepared samples gave the following analysis:

(a) K, 18.9; Ca, 20.7% or the solid sample contained K, 3.9; Ca 4.2 m mole/g.
(b) K, 25.9; Ca, 25.6; MA', 57.9%; 1g of sample contained K, 4.25; Ca, 4.1; MA', 12.8 m mole.

Theoretical values for K Ca (MA')$_3$, K, 23.1; Ca, 23.7; MA', 53.2%. 1g of material contains K, 5.9; Ca, 5.9; MA', 17.2 m mole. For K$_2$Ca(MA')$_4$ theoretical values are K, 32.8; Ca, 16.8; MA', 50.4%. 1g of material contains K, 8.38; Ca, 4.19; MA', 16.76 m mole. The white solid appears to be one in which the K:Ca ratio is unity, and is most probably KCa(MA')$_3$. The variability of results may be related to the stability of methylamine solvates under vacuum, a feature already noted for simple calcium dimethylamide.

A solution (initial K, 0.5; Ca, 0.25 m mole/g) stored for 1 day and from which white solid had been removed had an exchange rate of 73 min$^{-1}$, and after 2 days had reached a value of 13.5 min$^{-1}$. The solute in the latter case contained K, 0.24; Ca, 0.07; MA', 0.48 m moles/g. It retained its composition after treatment at 1000 psi hydrogen partial pressure.

1.3 Potassium barium methylamide

Barium metal dissolved readily in PMA in methylamine in much the same manner as strontium, i.e., with effervescence and formation of a blue solution. After 12 hrs some fine white powder (impurity from the Ba metal) was filtered out to give a solution which had an exchange rate of 76 min$^{-1}$ at 70° C. Analysis showed that the solution at 20° C contained K, 0.45; Ba, 0.26; MA', 0.94 m moles/g. The ratio K:Ba:MA' was 1.7:1.0:3.6. This is consistent with a mixture of Ba(MA')$_2$; 2KMA', or a salt K$_2$Ba(MA')$_4$.

On separate samples it was shown:
(a) That at −70° C solute separated from solution. This solid analyzed to give the ratio K:Ba:MA' as 0.91:1.0:3.0, suggesting it was KBa(MA')$_3$.
(b) That the solution at 20° C gave no reaction with hydrogen at 600 psi pressure.

1.4 Sodium strontium methylamide system

Strontium metal (.92 g, 10.5 m mole) was treated with sodium methylamide solution (24 g, 34 mls of a 0.88 m mole/g solution, 21 m mole). Reaction at −10° C overnight gave a very pale straw coloured supernatant solution over a white solid. Addition of dry methylamine (26.0 mls, designed to give a homogeneous system containing Na, 0.5; Sr, 0.25 m moles/g) did not give complete dissolution. The system was separated into:
(a) A white solid (1.056 g) which contained Na, 5.17; Sr, 6.23; MA', 1.3 m mole/g. The methylamine level is undoubtedly very low, probably due to exothermic reaction during ethanolysis, and
(b) a very pale yellow solution. This solution gave an exchange rate of 1 min$^{-1}$ and contained by analysis the following: Na, 0.3; Sr, 0.15; MA', 0.59 m moles/g.

1.5 Lithium strontium methylamide system

Strontium metal dissolved readily at −20° C in lithium methylamide solution to give a deep blue solution. At 20° C blue colouration was present only in the vicinity of the metal, and there was very noticeable gas effervescence.

Strontium metal (0.92 g, 10.5 m moles) was treated with a stock solution of lithium methylamide (10 mls, 7.5 g, of a 2.8 molal solution, 21 m moles). The system was blue and there was rapid effervescence. After 6 hrs the system was comprised of an almost colourless (faintly grey) system with a small quantity of white powder (which was the same as that powder in the K/Sr systems, judged to have come from coating of the strontium metal). At this point the system by preparation contained Li, 1.0 and Sr, 0.5 m moles/g.

The solution was diluted to Li 0.5; Sr, 0.25 m moles/g and filtered. The filtrate gave an exchange rate of 1 min$^{-1}$, and showed no reaction with hydrogen at a partial pressure of 600 psi.

The effect of pyrrolidine on this system was not established.

Potassium strontium methylamide systems 2.1 Dipotassium strontium tetramethylamide — solution systems which by preparation contain K, 0.5; Sr, 0.25 m moles/g.

Strontium metal reacted rapdily with PMA at −10° C to give a pale green/yellow solution which was stable at 20° C. The system contained a small quantity of fine white powder judged to be impurities of the coated strontium metal. To obtain samples free of this material was difficult, but could be achieved:
(a) by very careful filtration where the first few mls of filtrate were discarded or
(b) by storing the solution in a dip-tube vessel followed by careful sample removal.

A combination of both techniques was found desirable for larger preparation.

2.2 A solution which gave an exchange rate of 176 min$^{-1}$ contained a solute, analysis of which showed the original solution to contain K, 0.47; Sr, 0.17; MA', 1.12 m moles/g.

2.3 A solution which gave an exchange rate of 166 min$^{-1}$ contained K, 0.49; Sr, 0.25; MA', 1.01 m mole/g. The ratio K:Sr:MA' was, 2:1:4. K$_2$Sr(MA')$_4$ requires K:Sr:MA', 2:1:4. This system on addition of pyrrolidine (0.75 m mole/g) gave an exchange rate of 277 min$^{-1}$ and contained K, 0.49; Sr, 0.25; MA'. 0.69; pyrrolidide, 0.25 m mole/g. The addition of the pyrrolidine has caused formation of pyrrolidide anion and reduction of the methylamide anion level. Both in the presence and absence of pyrrolidine no hydride was formed, based on visual testing at 600 psi hydrogen partial pressure.

2.4 A solution which gave an exchange rate of 94.5 min$^{-1}$ contained K, 0.35; Sr, 0.20 m mole/g. Addition of pyrrolidine (0.3 m mole/g) gave a rate of 116 min$^{-1}$, and the system contained K, 0.35; Sr, 0.20; MA', 0.08 and pyrrolidide, 0.22 m moles/g.

2.5 A solution which gave an exchange rate of 117 min$^{-1}$ contained K, 0.5; Sr, 0.37 m mole/g. Addition of pyrrolidine (2 m mole/g) gave a rate of 162 min$^{-1}$ and the system contained K, 0.5; Sr, 0.23; MA', 0.2, and pyrrolidide, 0.88 m mole/g.

2.6 K$_2$Sr(MA')$_4$ — system containing 0.75 m moles/g Concentration of the methylamide system described in section 2.4 gave a yellow brown solution. Its viscosity was judged to be slightly higher than its parent solution. The system, which remained homogeneous on cooling to −70° C, had an exchange rate of 153 min$^{-1}$ and contained K, 1.7 and Sr 0.65 m moles/g. The addition of pyrrolidine (3.7 m mole/g) gave a rate of 124.4 min$^{-1}$ and the solution contained K, 1.7; Sr, 0.65; MA', 0.24; and pyrrolidide, 3.1 m moles/g.

2.7 K/Sr solution system containing K, 0.5; Sr 0.1 m moles/g

The preparation and appearance of the solution was the same as that described in section 2.1. A solution which had an exchange rate of 107 min$^{-1}$ contained K, 0.37; and Sr, 0.09 m moles/g. The addition of pyrrolidine (0.7 m moles/g) gave a rate of 170 min$^{-1}$, and in the presence of more pyrrolidine (1.4 m mole/g total), the rate was 194.4 min$^{-1}$. The latter solution contained K, 0.37; Sr, 0.09; MA', 0.07; pyrrolidide, 0.46 m moles/g. These systems gave no precipitate at 600 psi hydrogen partial pressure.

2.8 Systems containing by preparation, K, 0.5; Sr, 0.5 m mole/g

Although strontium metal (1.84 g, 21 m mole) reacted readily with PMA (60 mls, 42 g, 21 m mole) at 20° C, the system after 24 hrs contained a substantial quantity of white granular reaction product (1.87 g) (based on the amounts of Sr and PMA used, the total reaction product PMA + Sr(MA') = 1.38 + 2.94 g = 4.32 g). Analysis of the solid showed it contained MA', 20.38 m moles or 10.9 m moles/g. The filtrate which had an exchange rate of 118 min$^{-1}$ contained K, 0.37, Sr, 0.27; MA', 1.10 m mole/g. The amounts of K and Sr not in solution would therefore be K, 0.13; Sr, 0.23 m mole/g. This is equivalent to PMA solid 0.36 g and Sr (MA')$_2$ solid 1.3 g, total, 1.66 g. This compares well with the actual amount of precipitate filtered from the solution (1.87 g).

Potassium beryllium methylamide system 3.1 Beryllium powder (90 mg, 10.05 m mole) was treated with PMA (42 g of 0.5 m mole/g solution) at 20° C. After 4 weeks some unchanged Be (33.2 mg) was removed from the system, which was pale green — yellow. This solution which contained by preparation K, 0.55 m mole/g and Be, 0.16 m mole/g gave an H-D cell exchange rate of 132 min$^{-1}$.

The results are summarized in Table 1.

TABLE 1

| Metal Mixture | | Approximate Metal Level m mole/g | | Exchange Rates, Min $^{-1}$(1) | | Hydrogenolysis 600 psi |
|---|---|---|---|---|---|---|
| Group I | Group II | Group I | Group II | A | B | Hydrogen |
| K | Be | 0.5 | 0.15 | 132 | — | negative |
| K | Mg | 0.3 | 0.7 | 4 | — | " |
|   |   | 0.4 | 0.4 | 9 | — | " |
| K | Ca | 0.5 | 0.25 | 132 | — | " |
|   |   | 0.2 | 0.1 | 135 | — | " |
| K | Sr | 0.5 | 0.2 | 176 | — | " |
|   |   | 0.5 | 0.25 | 166 | 277 (.75) | " |
| K | Sr | 0.4 | 0.2 | 94.5 | 116 (.3) | " |
| K | Sr | 0.4 | 0.1 | 107 | 170 (.7); 194.4 (1.4) | " |
| K | Sr | 1.7 | 0.65 | 153 | 124.4 (3.7) | " |
| Li | Sr | 0.5 | 0.25 | <1 | — | " |
| Na | Sr | 0.3 | 0.15 | <1 | — | " |

TABLE 1-continued

| Metal Mixture | | Approximate Metal Level m mole/g | | Exchange Rates, Min$^{-1}$(1) | | Hydrogenolysis 600 psi |
|---|---|---|---|---|---|---|
| Group I | Group II | Group I | Group II | A | B | Hydrogen |
| K | Ba | 0.5 | 0.25 | 76 | — | " |

H-D exchange rate in laboratory cell at −70° C Potassium methylamide control (0.5 m mole/g) gave an exchange rate of 100 min$^{-1}$. Data (exchange rates) under column A refers to the methylamide systems alone, column B refers to systems containing pyrrolidine, the level of which in m mole/g is indicated in the bracket ( ).

I claim:

1. In a process for catalyzed H-D exchange between hydrogen and an amine in a deuterium enrichment process, the improvement comprising utilizing as catalyst in the amine phase a dissolved composite amide including both Group I metal and Group II metal amides, the composite catalyst being selected to provide at least one of an increased H-D exchange rate or prolonged activity over that of the single Group I metal amide.

2. The process of claim 1 wherein the amine comprises an alkylamine and the amides comprise alkylamides.

3. The process of claim 2 wherein the alkyl group is methyl and the Group I metal is potassium.

4. The process of claim 1 wherein the Group II metal is selected from beryllium, calcium and strontium.

5. The process of claim 1 wherein the composite amide is a potassium-strontium amide.

6. The process of claim 1 wherein the Group II metal is present in an effective amount up to about equimolar with the Group I metal.

7. The process of claim 1 wherein the Group II metal is present in about 30 – 60 mole % based on the Group I metal.

8. The process of claim 1 wherein pyrrolidine is added in amounts increasing the H-D exchange rate.

9. A composite catalyst for the exchange of deuterium between hydrogen and an amine, comprising an amine-soluble mixed metal amide including metals from Group I and Group II, the composite amide being selected to have at least one of an increased H-D exchange rate, or prolonged catalytic activity, over that of the single Group I metal amide.

10. The catalyst of claim 9 wherein the amides comprise metal alkylamides.

11. The catalyst of claim 9 wherein the alkyl group is methyl and the Group I metal is potassium.

12. The catalyst of claim 9 wherein the Group II metal is selected from beryllium, calcium and strontium.

13. The catalyst of claim 9 wherein the mixed metal amide is a potassium-strontium amide.

14. The catalyst of claim 9 wherein the Group II metal is present in an effective amount up to about equimolar with the Group I metal.

15. The catalyst of claim 9 wherein the Group II metal is present in about 30 – 60 mole % based on the Group I metal.

16. The catalyst of claim 9 dissolved in the corresponding amine.

17. The catalyst of claim 9 in combination with pyrrolidine in amounts increasing the H-D exchange rate.

* * * * *